US007888015B2

(12) United States Patent
Toumazou et al.

(10) Patent No.: US 7,888,015 B2
(45) Date of Patent: Feb. 15, 2011

(54) QPCR USING SOLID-STATE SENSING

(75) Inventors: Christofer Toumazou, London (GB);
Sunil Purushothaman, London (GB)

(73) Assignee: DNA Electronics Ltd., London (GB)

( * ) Notice: Subject to any disclaimer, the term of this patent is extended or adjusted under 35 U.S.C. 154(b) by 0 days.

(21) Appl. No.: 11/681,212

(22) Filed: Mar. 2, 2007

(65) Prior Publication Data
US 2008/0032295 A1 Feb. 7, 2008

Related U.S. Application Data

(63) Continuation-in-part of application No. 10/471,197, filed as application No. PCT/GB02/00965 on Mar. 11, 2002.

(30) Foreign Application Priority Data
Mar. 9, 2001 (GB) ................................. 0105831.2

(51) Int. Cl.
*C12Q 1/68* (2006.01)
(52) U.S. Cl. .......................... 435/6; 435/91.1; 435/91.2
(58) Field of Classification Search ........................ None
See application file for complete search history.

(56) References Cited

U.S. PATENT DOCUMENTS

| | | | |
|---|---|---|---|
| 4,777,019 A | 10/1988 | Dandekar | |
| 5,466,348 A | 11/1995 | Holm-Kennedy | |
| 5,543,024 A | 8/1996 | Hanazato et al. | |
| 5,632,957 A | 5/1997 | Heller et al. | |
| 5,827,482 A | 10/1998 | Shich et al. | |
| 6,015,714 A | 1/2000 | Baldarelli et al. | |
| 6,060,327 A | 5/2000 | Keen | |
| 6,413,792 B1 | 7/2002 | Sauer et al. | |
| 6,482,639 B2 * | 11/2002 | Snow et al. | 435/287.2 |
| 6,953,958 B2 | 10/2005 | Baxter et al. | |
| 7,049,645 B2 | 5/2006 | Sawada et al. | |
| 2003/0186262 A1 | 10/2003 | Cailloux | |
| 2004/0262636 A1 | 12/2004 | Yang et al. | |
| 2005/0032075 A1 | 2/2005 | Yaku et al. | |

FOREIGN PATENT DOCUMENTS

| | | |
|---|---|---|
| EP | 0 235 024 A2 | 9/1987 |
| JP | 01 102352 A | 4/1989 |
| JP | 02 309241 A | 12/1990 |
| WO | 90/13666 | 11/1990 |
| WO | 02/086162 A1 | 10/2002 |
| WO | 03/073088 A2 | 9/2003 |

OTHER PUBLICATIONS

Heid et al. Genome Research vol. 6:986-994. 1996.*
Alphey, Luke, "DNA Sequencing: From Experimental Method to Bioinformatics," Bios Scientific Publishers Ltd., Oxford, United Kingdom, pp. i-xiv and 1-25 (1997).
Auroux et al., "Miniaturised nucleic acid analysis," Lab Chip, 4, pp. 534-546 (2004).
Blazej et al., "Microfabricated bioprocessor for integrated nanoliter-scale Sanger DNA sequencing," PNAS 103, pp. 7240-7245 (2006).
Buck, R., "Electrochemistry of Ion-Selective Electrodes," Sensors and Actuators, (1), pp. 197-260 (1981).
Hanzato et al., "Integrated Multi-Biosensors Based on an Ion-sensitive Field-Effect Transistor Using Photolithographic Techniques," IEEE Transactions Electron Devices, vol. 36, pp. 1303-1310 (1989).
Hon-Sumn Wong et al., "A Self-Contained CMOS Integrated pH sensor," Electronic Devices Meeting (1988).
Iordanov, V. et al., Sensorized nanoliter reactor chamber for DNA multiplication, IEEE, pp. 229-232 (2004).
Lee, Jeong-Gun et al., "Microchip-based one step DNA extraction and real-time PCR in one chamber for rapid pathogen identification," The Royal Society of Chemistry, Lab Chip, 6, pp. 886-895 (2006).
Matsuo, M. Esashi, "Methods of ISFET fabrication," Sensors and Actuators, 1, pp. 77-96 (1981).
Matthews, C. et al., "Biochemistry, $3^{rd}$ Edition," Addison Wesley Longman, Inc. Benjamin/Cummings, pp. i-xxviv, 57-125 and 980-1026 (2000).
Patent Abstracts of Japan vol. 013, No. 342 (P-908), Aug. 2, 1989 and JP 01 102352 A (Toshiba Corp), Apr. 20, 1989 abstract.
Patent Abstracts of Japan vol. 015, No. 095 (P-1176), Mar. 7, 1991 and JP 02 309241 A (Matsushita Electric Ind Co Ltd), Dec. 25, 1999 abstract.
PCT Notification of Transmittal of the International Search Report or the Declaration for PCT Counterpart Application No. PCT/EP2007/052010 Containing International Search Report (Sep. 5, 2007).
Purushothaman et al., "Towards Fast Solid State DNA Sequencing," IEEE IV-169-172 (2002).
Purushothaman, S. et al., "Protons and single nucleotide polymorphism detection: A simple use for the Ion Sensitive Field Effect Transistor," Sensors and Actuators B 114, pp. 964-968 (2006).
Sakata and Miyahara, "Direct detection of Single-base Extension reaction Using genetic Field effect Transistor," Proceedings of the $3^{rd}$ Annual Internationa IEEE EMBS Special Topic Conference on Microtechnologies in Medicine and Biology Microtechnology in Medicine and Biology, 12-15, pp. 219-222 (May 2005).
Sakata and Miyahara, "Potentionmetric Detection of Single Nucleotide Polymorphism by Unisng a Genetic Field-Effect Transistor," ChemBio Chem 6, pp. 703-710 (2005).
Sakata et al., "Direct transduction of allele-specific primer extension into electrical signal using genetic field effect transistor," Biosensors & Bioelectronics, Elsevier Science Publishers, Barking, GB, vol. 22, No. 7, pp. 1311-1316 (2007) (XP022022958).
Sakata et al., "Immobilization of oligonucleotide probes on $Si_3N_4$ surface and its application to genetic field effect transistor," Materials Science and Engineering C 24, pp. 827-832 (2004).

(Continued)

Primary Examiner—Heather Calamita
(74) Attorney, Agent, or Firm—Nixon & Vanderhye P.C.

(57) ABSTRACT

Use of a pH sensor comprising an ion-sensitive field effect transistor (ISFET) to perform real time detection/quantification of nucleic acid amplification, e.g. polymerase chain reaction (PCR) nucleic acid amplification, based on detection of protons released during the primer extension phase.

20 Claims, 9 Drawing Sheets

OTHER PUBLICATIONS

Sakurai T. et al., "Real-Time Monitoring of DNA Polymerase Reactions by a Micro Isfet PH Sensor," Analytical Chemistry, American Chemical Society, Columbus, US, vol. 64, No. 17, pp. 1996-1997 (1992) (XP009015113).

Shakhov, Y. et al, "A Sensitive and Rapid Method for Determination of Pyophosphate Activity," Acta Chemica Scandinavica B 36, pp. 689-694 (1982).

Shiddiky et al., "Analysis of Polymerase chain reaction amplifications through phosphate detection using an enzyme-based microbiosensor in microfludic device," Electrophoresis 27, pp. 1-9 (2006).

Shoffner et al., "Chip PCR. I. Surface passivation of microfabricated silicon-glass chips for PCR," Nucleic Acids Research, vol. 24, No. 2, pp. 375-379 (1996).

Starodub, N. F. et al., "Optimisation methods of enzyme integration with transducers for analysis of irreversible inhibitors," Sensors and Actuators B, 58, pp. 420-426 (1999).

Sterky, F. et al., "Squence of genes and genomes," Journal of Biotechnology, vol. 76, pp. 1-31 (2000).

Tabor, S. et al., "DNA Sequence analysis with a modified bacteriophage T7 DNA polymerase. Effect of pyrophosphorolysis and metal ions," Journal of Biological Chemistry, pp. 8322-8328 (1990).

Tsuruta H. et al., "Detection of the products of apolymerase chain reaction by an ELISa system based on an ion sensitive field effect transistor," Journal of Immunological Methods, Elsevier Science Publishers B. V., Amsterdam, NL, vol. 176, No. 1, pp. 45-52 (1994) (XP009021947).

Tsuruta H. et al., "Quantitation of IL-Ibeta mRNA by a combined method of RT-PCR and an ELISA based on ion-sensitive field effect transistor," Journal of Immunological Methods, Elsevier Science Publishers B. V., Amsterdam, NL, vol. 180, No. 2, pp. 259-264 (1995) (XP004021048).

Victorova, L. et al., "New substrates of DNA polymerases," Federal of European Biochemical Societies Letters, 453, pp. 6-10 (1999).

Woias, P., et al., "Modelling the short-time response of ISFET sensors," Sensors and Actuators B, 24-25, pp. 211-217 (1995).

Zhang et al., "PCR microfluidic devices for DNA amplification," Biotechnology Advances, 24, 243-284 (2006).

\* cited by examiner

DNA template

GCCTGCTGC    SEQ ID NO: 1

QPCR USING SOLID-STATE SENSING

CROSS-REFERENCE TO RELATED APPLICATIONS

The present application is a continuation-in-part of U.S. patent application Ser. No. 10/471,197, filed Mar. 2, 2004, which is the national phase application of International Patent Application no. PCT/GB02/00965, filed Mar. 11, 2002, which claims priority from GB Patent Application no. 0105831.2, filed Mar. 9, 2001

FIELD OF THE INVENTION

The present invention relates to a sensing apparatus and method, and particularly though not exclusively to a sensing apparatus and method suitable for DNA sequence determination, which can has also been extended for quantitative real time monitoring of nucleic acid amplification, e.g. polymerase chain reaction (PCR) amplification, ligase chain reaction or transcription mediated amplification. Quantitative real time polymerase chain reaction (qPCR or RT-PCR) has become a de facto standard for amplification of low amounts of DNA or RNA, e.g. for cloning of gene sequences, forensic testing and genetic testing for disease-linked mutations. Most embodiments of qPCR require labelled probes (e.g. fluorescent dyes) to detect amplicons. qPCR disclosed herein avoids the need for labelled probe. It relies instead on pH sensitive ISFET sensing of proton release consequent to PCR cycling and can thereby be performed on a chip.

BACKGROUND TO THE INVENTION

The inventors first found that ISFETs can be used to monitor local fluctuations in ionic charge corresponding with discrete chemical events, more particularly for example proton release associated with individual nucleotide insertion at the end of an oligonucleotide chain. Monitoring of individual nucleotide insertions by a pH sensitive ISFET may be utilised in DNA sequencing based on conventional Sanger method DNA sequencing and in identifying allelic variants, e.g. single nucleotide polymorphisms (SNPs), relying on detecting extension of oligonucleotide primers designed to target specific nucleic acid sites. The inventors further realised that protons are also a PCR product and that qPCR may therefore also be achieved by ISFET monitoring of proton release, preferably in a low reaction volume chamber DNA sequencing methods have remained largely unchanged in the last 20 years [Sterky and Lundberg, 'Sequence analysis of genes and genomes', J. Biotechnology (2000) 76, 1-31]. The Sanger method is a well-known method of DNA sequencing, and comprises DNA synthesis with termination of DNA replication at points of di-deoxynucleotide insertion. The DNA synthesis is followed by electrophoresis of the synthesised DNA to separate DNA molecules according to their mass to charge ratios, thereby allowing determination of the DNA sequence. A disadvantage of the Sanger method is that electrophoresis is complex, costly and hazardous. It is an object of the present invention to provide a sensing apparatus and method whereby Sanger-type sequencing employing di-deoxynucletide triphosphates can be carried out without need for separation of extended oligonucleotide strands. However, as indicated above, the invention can be applied more broadly to monitoring of any chemical event which will give rise to a fluctuation in ionic charge, e.g. proton release. Sensing devices comprising a pH sensitive ISFET are now also proposed for use in carrying out label free qPCR in small (nano) volumes.

SUMMARY OF THE INVENTION

According to a first aspect of the invention, there is provided a sensing method comprising detecting an electrical signal output from an ion sensitive field effect transistor (IS-FET), and monitoring the detected electrical signal to discriminate localised fluctuations of ionic charge, the localised fluctuations of ionic charge occurring at or adjacent the surface of the field effect transistor indicating events occurring during a chemical reaction. More particularly, there is provided a method of observing reaction intermediaries during a chemical reaction and comprising detecting an electrical signal output from an ISFET exposed to said reaction, and monitoring the detected electrical signal to discriminate discrete fluctuations in the electrical signal, the discrete fluctuations indicating reaction intermediaries occurring during a chemical reaction. In a preferred embodiment, said reaction intermediaries arise from one or more nucleotide insertions at the end of a nucleotide chain in a DNA synthesis and individual nucleotide insertions are monitored through detecting change in the detected electrical signal consequent upon proton release with each nucleotide insertion.

The inventors have realised that localised fluctuations of ionic charge which occur at the surface of a field effect transistor may be measured. Although ion sensitive field effect transistors are already known, they have previously been used to monitor slow changes of for example absolute values of pH in a reaction mixture as a whole. They have not been used to monitor localised fluctuations of ionic charge associated with individual chemical events such as nucleotide addition to a DNA. In known application of an ion sensitive field effect transistor arrangement, a measurement of the absolute value of the pH of the reaction mixture is made every 30 seconds. Typically, many millions of chemical reactions will occur between measurements, and this is seen as a change of the absolute value of the pH. The invention allows individual chemical events to be monitored.

Preferably, the chemical reaction is DNA synthesis, and the fluctuations of ionic charge indicate the insertion of individual di-deoxynucleotide triphosphates (ddNTPs) and deoxynucleotide triphosphates (dNTPs).

A limitation of existing ion sensitive field effect transistor arrangements is that they attempt to measure absolute values of pH and consequently suffer from drift and hysteresis. The invention monitors fluctuations of ionic charge rather than absolute values, and thus avoids this problem.

Preferably, the time at which the fluctuations occur and the magnitude of the fluctuations is monitored to allow sequence determination of DNA.

According to a second aspect of the invention there is provided a sensing apparatus comprising an ion sensitive field effect transistor arranged to generate an electrical output signal in response to localised fluctuations of ionic charge at or adjacent the surface of the transistor, means for detecting an electrical output signal from the ion sensitive field effect transistor, and means for monitoring the detected electrical signal to discriminate localised fluctuations of ionic charge, the localised fluctuations of ionic charge indicating events occurring during a chemical reaction.

Again, preferably, the chemical reaction is DNA synthesis, and the localised fluctuations of ionic charge indicate the insertion of individual di-deoxynucleotide triphosphates (ddNTP) and deoxynucleotide triphosphates (dNTP). Preferably, the monitoring means is arranged to monitor the time at which the localised fluctuations occur and the magnitude of the localised fluctuations, to allow sequence determination of DNA.

In a further aspect of the invention, there is provided a method of monitoring nucleic acid amplification, e.g. qPCR, in a sample by ISFET detection of pH change. More particularly, there is provided a method of monitoring nucleic acid amplification in a sample comprising a buffered nucleic acid amplification mixture for amplification of target sequence if present in the sample, characterised in that said monitoring is by means of detecting change of pH resulting from proton release in the presence of target sequence as amplification proceeds beyond a threshold number of cycles for buffering capacity of the sample to be overcome, said detecting employing a sensing apparatus comprising an ISFET having a sensing surface exposed to the sample and arranged to generate an electrical output signal in response to change of pH at said transistor surface and means for detecting an electrical output signal from the ISFET. To achieve the required degree of sensitivity in detection, amplification will preferably be carried out in small (preferably nano) volumes and at low buffer capacity such that the number of protons released leads to rapid change in pH as the buffer capacity of the sample is overcome. Thus such a method may advantageously be carried out in a nanoreactor with integrated pH sensitive ISFET provided in a microfluidic device or chip.

BRIEF DESCRIPTION OF THE DRAWINGS

Specific embodiments of the invention will now be described by way of example only with reference to the accompanying figures, in which.

DETAILED DESCRIPTION

Figure 6:
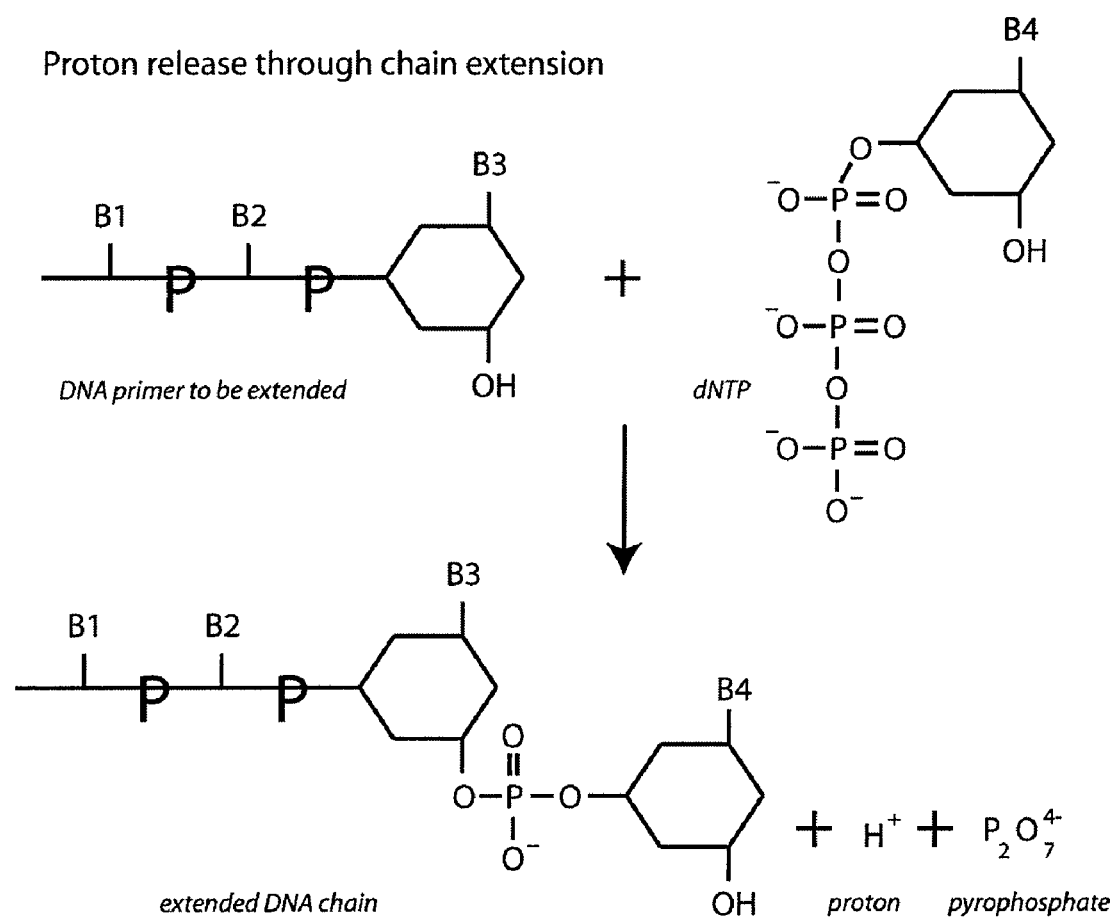
FIG. 6 shows proton release through DNA extension monitored in applying the invention to DNA sequence determination.

DNA sequencing of the Sanger-type using an embodiment of the invention is performed as follows: A quantity of DNA of interest is amplified using either a polymerase chain reaction or cloning, and the region of interest is primed so that DNA polymerase catalyses DNA synthesis through the incorporation of nucleotide bases in a growing DNA chain thereby releasing hydrogen ions; see FIG. 6.

Figure 1:
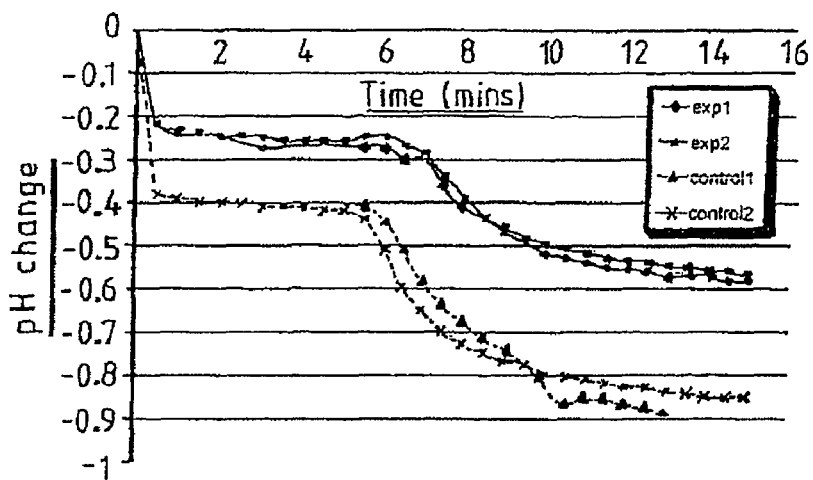
FIG. 1 shows pH changes occurring during DNA chain extension using a buffered reaction medium.

The results shown in FIG. 1 demonstrate the DNA extension reaction and its effect on pH. The pH was measured using a glass electrode arrangement, with measurements of the absolute value of pH taken every 30 seconds. The pH can be seen to fall gradually. The embodiment of the invention uses this reaction to monitor nucleotide insertion, by detecting localised fluctuations of pH which occur at or adjacent the surface of an ion sensitive field effect transistor.

The ISFET is provided with an ion sensitive silicon nitride layer, on top of which a layer of polymerase is provided. The release of protons from nucleotide insertion during the DNA extension reaction is detected by the ISFET. The magnitude of pH change in either direction (i.e. positive or negative) is detected in order to reliably detect nucleotide insertion, as described below. Individual nucleotide insertion will occur approximately every 3 ms at a temperature of 65° C., [Tabor and Richardson, 'DNA Sequence Analysis with a Modified bacteriophage T7 DNA polymerase. Effect of pyrophosphorolysis and metal ions', J. Biol. Chem. (1990) 14, 8322-8328.]. The ISFET is able to detect rapid pH changes and has an immediate response rate measured to be within 1 ms of a pH change [Woias et al., 'Modelling the short-time response of ISFET sensors', Sensors and Actuators B, 24-25 (1995), 211-217].

The follow-up reactions which succeed nucleotide insertion are pH-dependent, and therefore net consumption or production of hydrogen ions depends on the pH in which the reaction occurs. Generally, the reaction is conducted in the pH range 6 to 8.5, e.g. 7 to 7.5. In this range, hydrogen ions are overall liberated during nucleotide insertion. The embodiment of the invention thus monitors drops in pH as indicators of nucleotide insertion.

Figure 2:
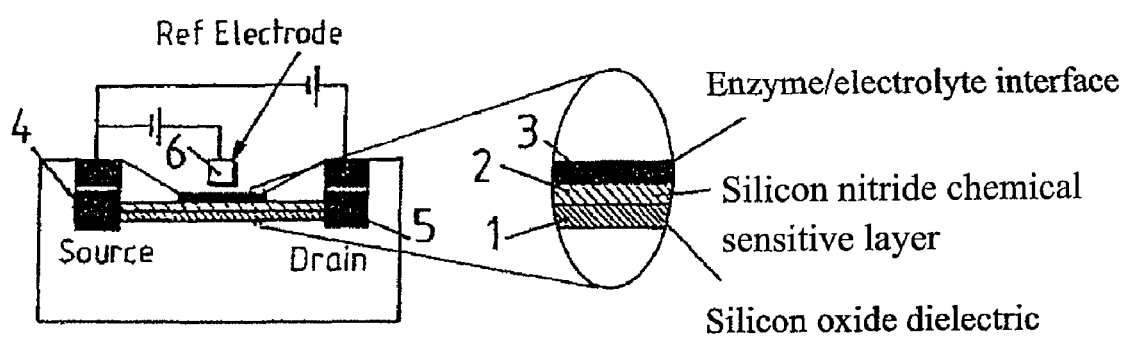
FIG. 2 is a schematic diagram of a field effect transistor which embodies the invention.

A pH sensitive FET which embodies the invention is shown in FIG. 2. The FET is similar to a traditional MOSFET (Metal Oxide Semiconductor Field Effect Transistor). The FET comprises a silicon oxide dielectric layer 1, a silicon nitride chemical sensitive layer 2, and an enzyme/electrolyte interface 3. The layers 1, 2 and interface 3 are located between a source 4 and drain 5 (the conventional configuration of a FET). The FET is provided on a silicon chip, which is encapsulated in epoxy resin to protect it from the reagent mixture. The epoxy resin helps to protect the FET from hydration and charge migration [Matsuo and Esashi, 'methods of ISFET fabrication', Sensors and actuators, 1 (1981) 77-96]. The FET gate itself is not covered by epoxy resin, so that it may be immersed in the reagent mixture.

The enzyme/electrolyte interface 3 shown in FIG. 2 allows ion sensitivity of the silicon nitride layer 2 to be used for DNA sequencing. The FET functions by producing an exchange of charged ions between the surface of the chemical sensitive layer 2 and the reacting medium (i.e. the enzyme/electrolyte interface 3):

$$SiOH \leftrightarrow SiO^- + H^+$$

$$SiOH_2^+ \leftrightarrow SiOH + H^+$$

$$SiNH_3^+ \leftrightarrow SiNH_2 + H^+$$

The inclusion of silicon nitride is advantageous because it provides increased and faster sensitivity to changes of pH than would be obtained in the absence of the silicon nitride. In addition the silicon nitride helps to protect the FET from hydration and charge migration.

A non-Nernstian response accounts for the immediate sensitivity of the FET, arising from rapid proton dependant binding and unbinding of charged ions at the insulating gate silicon nitride surface, which results in a reproducible variation in the voltage drop across the silicon nitride layer 2. The variation of the voltage drop across the silicon nitride layer 2 correlates with changes of pH. The voltage drop is monitored using instrumentation circuitry, thereby allowing the detection of individual nucleotide insertions. The measured voltage is referred to as the flatband voltage.

The enzyme/electrolyte interface 3 is deposited on the silicon nitride layer using a known enzyme linkage method [Starodub et al., 'Optimisation methods of enzyme intergration with transducers for analysis of irreversible inhibitors', Sensors and Actuators B 58 (1999) 420-426]. The method comprises pre-silanising the silicon nitride layer 2 using aminosilane solution, and then activating the surface using glutaraldehyde. A drop of buffer/polymerase enzyme solution is then deposited on the silicon nitride layer 2 and allowed to dry for about half an hour to form the enzyme layer 3.

The embodiment shown in FIG. 2 uses a reference electrode 6 to provide a measurement of pH changes. The reference electrode is relatively large and difficult to fabricate. An alternative embodiment of the invention does not use a reference electrode, but instead uses a second FET which has the same construction as the first FET, but is provided with a non-enzyme linked layer instead of the enzyme layer 3.

This configuration is advantageous because it provides a differential measurement which gives an improved signal to noise ratio.

Figure 3:
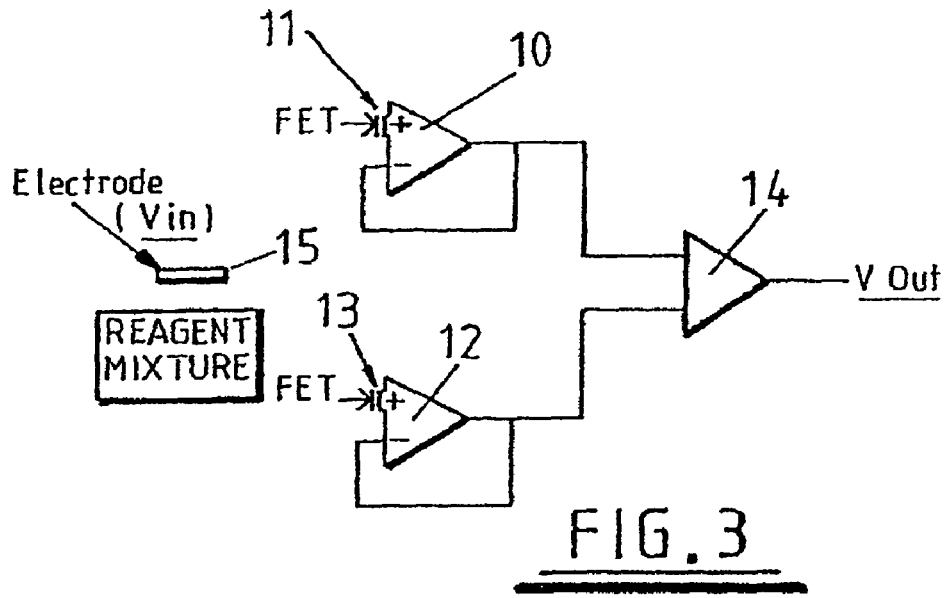
FIG. 3 is a schematic diagram of a pair of field effect transistors which embody the invention.

An alternative embodiment of the invention is illustrated in FIG. 3. The configuration of this embodiment is based upon a known construction [Wong and White, 'A self-Contained CMOS Integrated pH Sensor, Electron Devices meeting IEEE 1988] which has previously been used to monitor gradual slow drift of pH. The embodiment comprises a first operational amplifier 10 to which the source of the first FET 11 is connected (the first FET has the enzyme linked layer), and a second operational amplifier 12 to which the source of the second FET 13 is connected (the second FET has no-enzyme linked to the FET). The drains of the first and second FETs are connected to a fixed current source (not shown). Outputs from the first and second operational amplifiers are passed to a differential amplifier 14, which amplifies the difference between the outputs to generate an output signal Vout. Negative feedback from the differential amplifier 14 passes to a noble metal electrode 15 which is located in the reagent mixture. The operational amplifier 14 generates an output voltage which keeps the voltage applied to the FETs 11, 13 the same despite changes of hydrogen concentration.

The embodiment shown in FIG. 3 is advantageous because it allows rationalisation of fabrication of the FETs 11, 13 and the operational amplifiers 10, 12, 15.

The FETs 11, 13 may be arranged to form the first stage of the operational amplifiers 10, 12. This is done for each operational amplifier by replacing a conventional FET of a long tail pair located at the input of the operational amplifier, with the first or second FET 11, 13. This is advantageous because it allows the first and second FETs to form part of the amplification circuitry.

Figure 4:
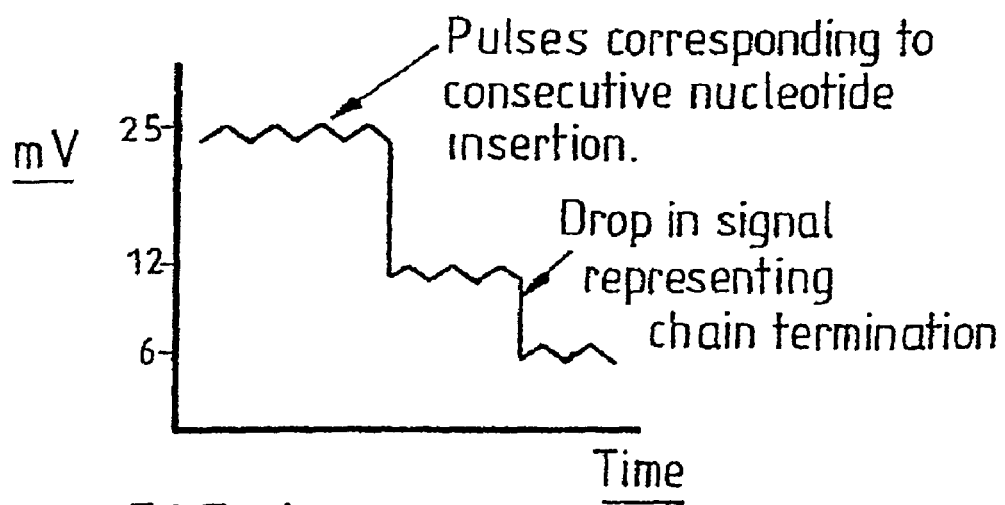
FIG. 4 is a schematic representation of results obtained using the pair of field effect transistors for DNA sequence determination of the Sanger type on a DNA template employing all required dNTPS and a single ddNTP in the reaction mixture.

A schematic example of a flatband voltage detected using the embodiment shown in FIG. 3 is illustrated in FIG. 4. The example is for an NMOS FET with the reaction operating in the ion consumption mode, as described above (the figure would be inverted for a PMOS FET or if the reaction was operating in the ion liberation mode).

The flatband voltage consists of pulses representing pH changes associated with nucleotide insertion and drops corresponding to ddNTP insertion and chain termination. The number of local pulses prior to a larger drop determines the number of bases present before termination at a known base; the magnitude of the larger drop is dependant on the ratio of ddNTP:dNTP used in the reagent mixture and is important due to the dependence of read length for that drop. Through repetition of the process four times in different reaction chambers containing each of the four ddNTPS separately, the complete sequence is delineated.

Referring to FIG. 4 in detail, DNA synthesis is performed with termination of DNA synthesis at points of di-deoxynucleotide insertion of thymine bases. Each individual nucleotide insertion causes the liberation of a hydrogen ion, and these are detected as pulses of the flatband voltage, as can be seen in FIG. 4. When the DNA chain reaches a thymine base, nucleotide insertion is prevented for some of the DNA chains, and the amount of hydrogen ion consumption drops leading to a drop in signal output.

DNA synthesis continues for those DNA chains which were not terminated at the thymine base, and this is seen as pulses of the flatband voltage at the new lower level.

The flatband voltage falls again when the DNA chain reaches a second thymine base (reflecting the fall in available target due to ddNTP addition), and then continues to pulse at the lower level.

The method may be used with or without thermocycling. For example, thermocycling may be used to facilitate optimisation, using taq polymerase as a sequencing enzyme [Alphey, L., 'DNA sequencing: from experimental methods to bioinformatics' BIOS Scientific Publishers, 1997]. The pH of the reagent mixture may be adjusted for example. A decrease of the pH will lead to the production of more hydrogen ions, but will also tend to inhibit the reaction. Trials have shown pH 6.8 to be a useful value of pH. Magnesium may be added to the reagent mixture to actuate the enzyme. The concentrations of the reagents may be modified. A typical thermocycling sequence is set out in Table 1.

TABLE 1

| Cycle Sequencing | | |
|---|---|---|
| Temperature | Duration | Function |
| 95° C. | 30 sec | Denaturing of DNA template |
| 55° C. | 30 sec | Annealing of primer |
| 72° C. | 60 sec | DNA extension and termination |

Operating within a thermal cycler enables multiple repetition of the sequencing process with minimal manipulation.

This allows signal to noise boosting and easier delineation of difficult to read regions such as GC rich regions or areas of single nucleotide repeats.

Recombinant T7 polymerase may be used instead of taq polymerase. Where T7 polymerase is used, this may provide increased speed and improved accuracy of monitoring nucleotide insertion.

The steps used to fabricate the ion sensitive FET are set out below:

Purified Silicon Substrate

ADDITION OF DOPANT: PRODUCTION OF p-TYPE SUBSTRATE

SURFACE OXIDATION: $SiO_2$ LAYER GENERATION

SOURCE/DRAIN DEFINITION AND IMPLANTATION

SILICON NITRIDE DEPOSITION USING LPCVD*

CONTACT FORMATION

PASSIVATION

*Low pressure Chemical Vapour Deposition

The FETs and in particular those shown in FIG. 3, and the amplification stages may be replaced or combined with PMOS transistors.

The length of DNA that can be sequenced will normally be limited by the signal to noise at distal bases as the signal decays with ddNTP insertion. Using PMOS FETs should allow extension of the read length, but may involve a possible compromise over the location of more proximal bases. Installation of two separate FET circuits, of the type shown in FIG. 3, one NMOS pair of FETs and one PMOS pair of FETs should provide the optimum read length. Biasing in weak inversion is possible, since the measurement to be made is of changes to output, rather than absolute values, and absolute linearity in signal amplification for signal analysis is not required.

Measurements may be repeated to provide improved signal to noise ratios.

Monitoring of Nucleic Acid Amplification

A pH sensitive FET in a sensing device format as shown in FIG. 2 or 3 may also be advantageously employed to monitor nucleic acid amplification. Such use of a pH sensitive FET will be further described below with reference to performing qPCR. However, it will be appreciated that a pH sensitive FET may be employed in the same manner to monitor any form of nucleic acid amplification including transcription mediated amplification (TMA) or ligase chain reaction (LCR).

Figure 5:
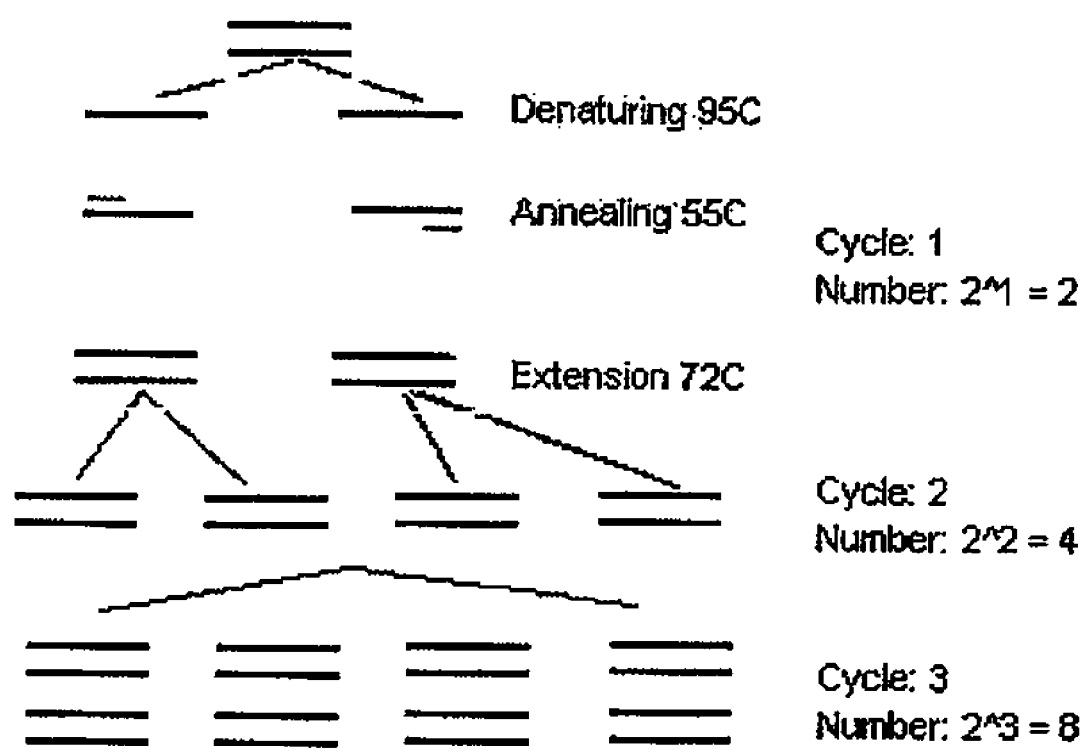
FIG. 5 shows diagrammatically PCR cycling resulting in amplification of a target nucleic acid sequence.

PCR is a process of amplification of a fragment of double-stranded DNA wherein primers are provided for hybridisation to each DNA strand to target a specific sequence of interest for amplification over a number of cycles of the amplification process. There are three stages to a PCR cycle as shown in FIG. 5. These are effected through thermal cycling in the presence of the necessary components for primer extension including a heat-resistant DNA polymerase as follows:

denaturing: the double-stranded template DNA is separated into two single strands due to the breaking of the hydrogen bonds that connect the two DNA strands, e.g. at 95° C.;

annealing: the sequence of interest is defined by two oligonucleotide primers which hybridise to the single strands of template DNA, carried out at e.g. 55° C.;

extension: DNA polymerase in the presence of dNTPs extends each primer, e.g. at 72° C.

Figure 7:
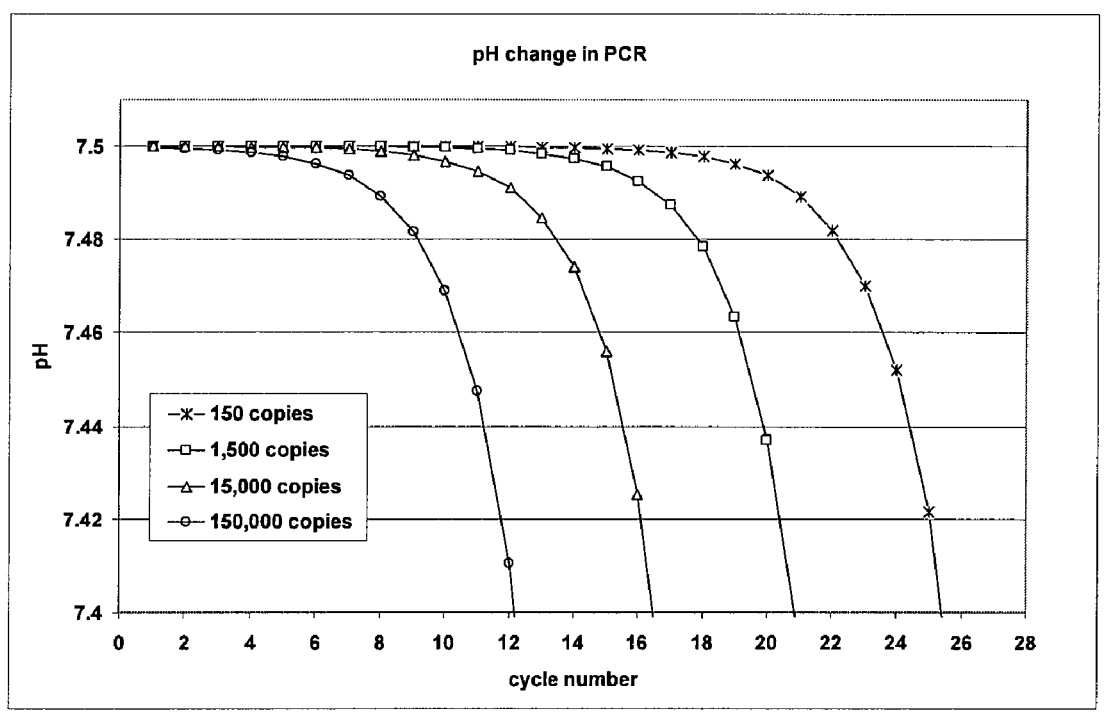
FIG. 7 shows results of simulated quantitative real time PCR using ISFET pH sensing.
Figure 8:
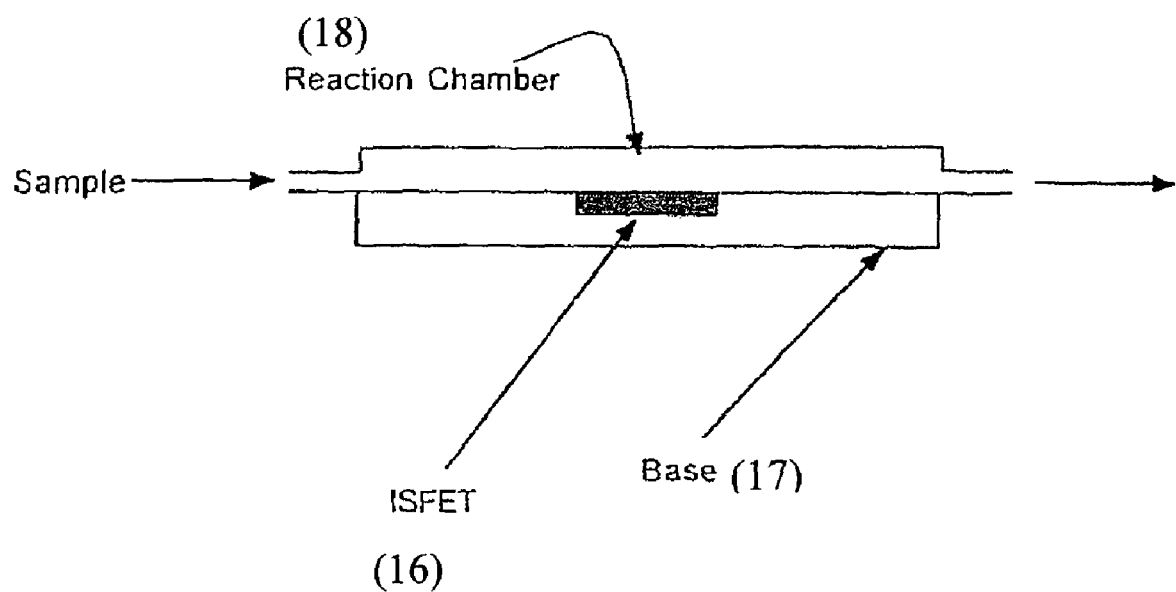
FIG. 8 is a schematic diagram of a microfluidic device containing an embedded ISFET in a low volume reaction chamber for carrying out qPCR.

In the extension stage of the cycle, protons are released consequent to base addition to each primer. It is this proton release which is used as the basis for real time quantification of PCR product in accordance with the invention. As noted above, the ISFET sensing surface will be exposed to buffered amplification mixture, preferably in a low volume reaction chamber or channel, e.g. a chamber or channel of a microfluidics device. Thus, for example, advantageously a low volume reaction chamber or well may be employed, e.g. of volume 1 pl to about 10 µl. This may overlay an ISFET as shown in FIG. 8 in which the ISFET (16) is embedded in the base (17) of the reaction chamber or well (18) and microchannels are provided for sample delivery and exit from the chamber. The chamber is capable of being heated and cooled between the annealing and denaturing temperatures (e.g. between 55 and 95° C.) for PCR thermocycling. Reagents for amplification such as the primers and dNTPs may be either dried inside the reaction chamber or introduced with the sample. If the target sequence is present, then this can be determined by the pH drop exceeding a certain threshold as the PCR cycles progress. If the target sequence is not present, the primers will not anneal to the template DNA and proton-releasing primer extension will not occur so that there is no significant change of pH. Due to the presence of buffer in the amplification mixture, pH change resulting from PCR cycling will initially be countered by buffer action. However, once the buffering capacity is overcome, rapid change in pH will be measurable as shown in FIG. 7. The number of cycles before the pH change passes a given threshold will depend on the DNA template concentration, the higher the concentration the fewer the cycles thereby allowing quantification of template DNA by calibrating the number of PCR cycles to reach the threshold against known template loads.

A number of ISFET-containing chambers as described above may be provided in a single microfluidic chip. This may be of particular benefit for example where amplification of short tandem repeats (STRs) is desired for DNA fingerprinting or where there is desire to amplify multiple DNA samples from the same source or different sources for genetic testing, or amplify different sites of one DNA strand. The ISFET, housed in a microfluidic chamber, may be an integral part of a chip such as a silicon chip with resistive on-chip heating elements and temperature sensors to control the temperature for DNA hybridisation and extension. Such a chip may also provide an integrated reference electrode and conductivity sensors.

Figure 9:
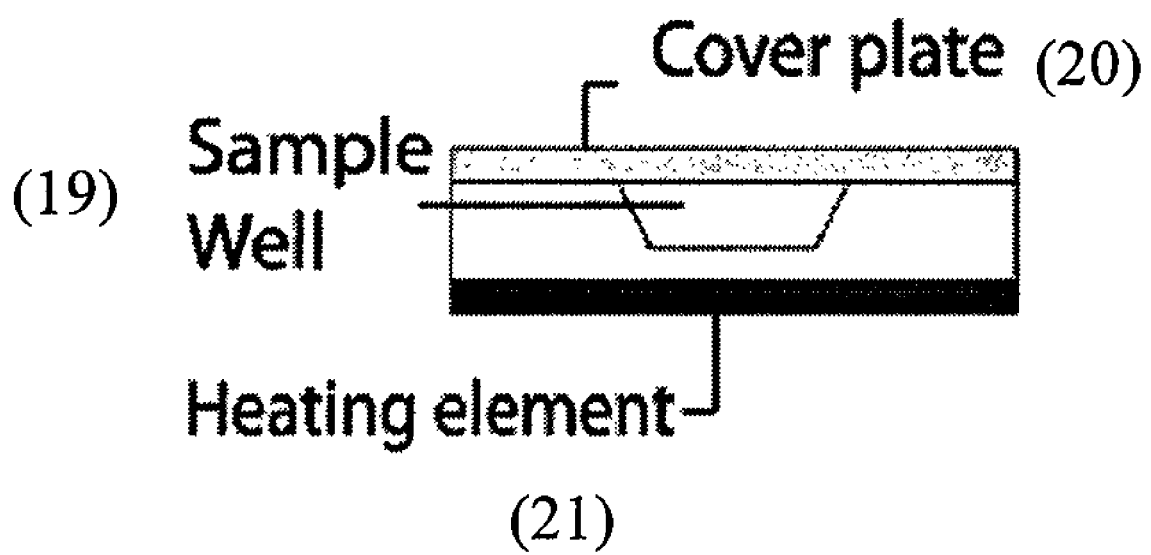
FIG. 9 is a further schematic view of a microfluidic device for carrying out PCR monitoring with a stationary sample in a reaction chamber/well (19) with cover (20). The chip may be heated by the heating element (21) and cooled to each required temperature in sequence for thermocycling of the sample.

Fabrication of one or an array of nanoliter reactor chambers in silicon with integrated actuators (heaters) for PCR monitoring has been described for example in Iordanov et al. 'Sensorised nanoliter reactor chamber for DNA multiplication, IEEE (2004) 229-232. Chambers thus fabricated (see FIG. 9) might each be provided with an integrated ISFET for monitoring of nucleic acid amplification in accordance with the invention. As noted by Iordanov et al. in their above-noted paper, untreated silicon and standard silicon-related materials are inhibitors of Taq polymerase. Therefore, when silicon or a silicon-related material, e.g. silicon germanium or strained silicon (all such materials will hereinafter be referred to as a silicon substrate) is employed for fabrication of a microchip chamber or channel for nucleic acid amplification it will usually be covered with material to prevent reduction of polymerase efficiency by the silicon such as SU8, polymethylmethacrylate (PMMA), Perspex™ or glass.

Surface passivation of microfabricated silicon-glass chips for PCR is also described by Shoffner et al. in Nucleic Acid Res. (1996) 24, 375-379. In their studies, silicon chips were fabricated using standard photolithographic procedures and etched to a depth of 115 μm. Pyrex™ glass covers were placed on top of each silicon chip and the silicon and glass were anodically bonded. Several types of surface passivations were investigated with a view to improving PCR amplification efficiency with thermo-cycling in the provided chamber. An oxidised silicon surface (SiO2) was found to give consistent amplifications comparable with reactions performed in a conventional PCR tube. Such a surface may also be favoured in fabricating a microfluidic device for carrying out nucleic acid amplification with ISFET pH sensing according to the invention. For further discussion of surface passivation in the fabrication of PCR microfluidic devices reference may be made to Zhang et al. 'PCR microfluidic devices for DNA amplification' in Biotechnology Advances (2006) 24, 243-284. As described in that review article, as an alternative to static surface passivation by substrate coating, it may be possible to include a passivation agent in the sample (dynamic passivation).

Figure 10:
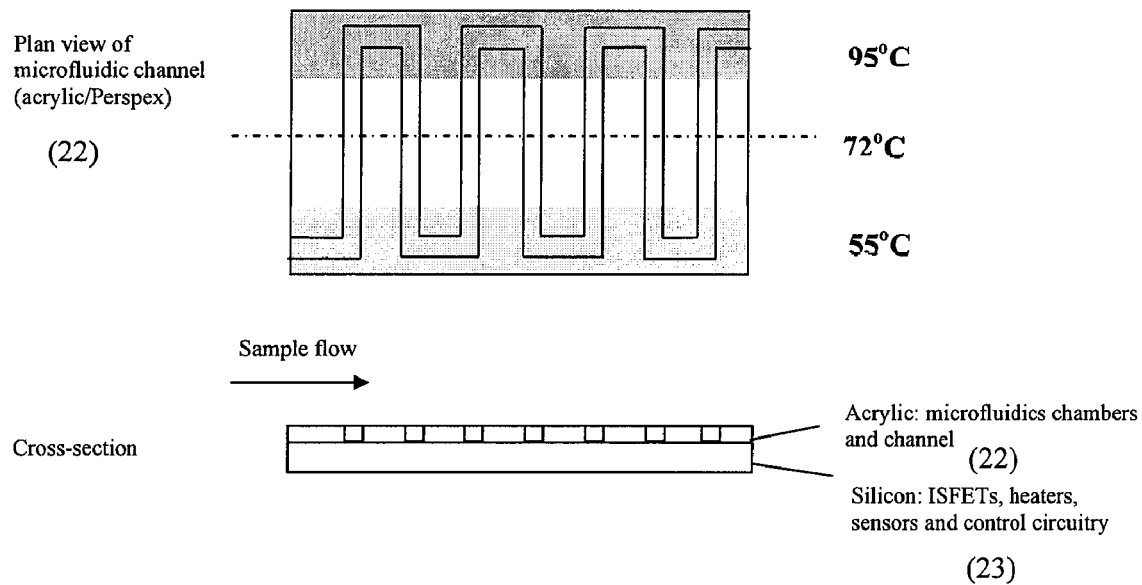
FIG. 10 shows a plan view and cross-section of a microfluidic device for carrying out PCR monitoring in accordance with the invention wherein the sample flows through a microfluidic channel (22), e.g. in a platform of acrylic or Perspex, which consecutively crosses zones of a silicon chip base (23) maintained at different temperatures for DNA denaturation, primer hybridisation to target and primer extension respectively. The three temperature zones for thermo-cycling of the sample for PCR are shown.
Figure 11:
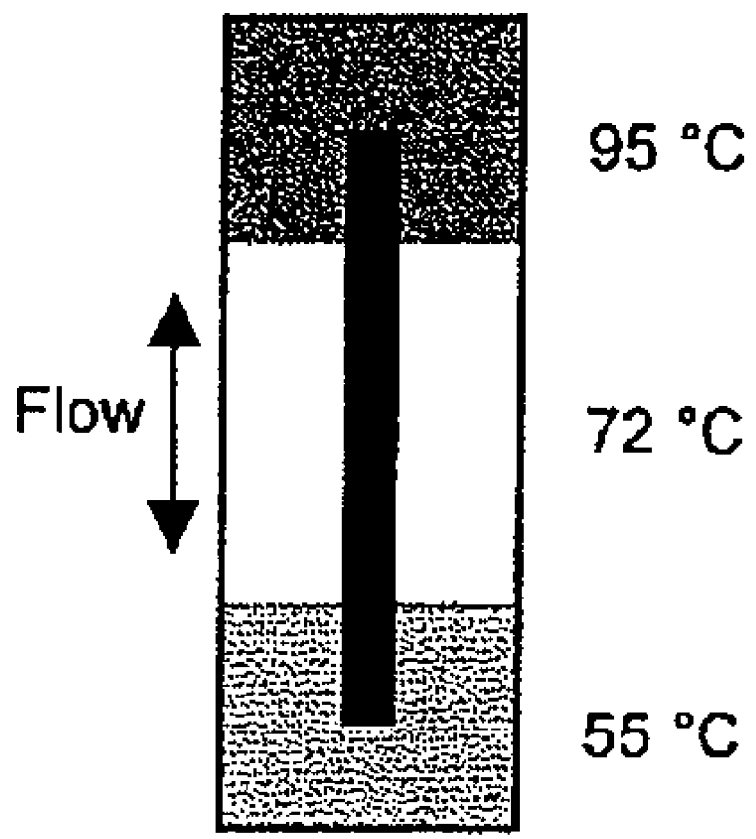
FIG. 11 is a schematic view of an alternative microfluidic device for monitoring PCR in accordance with the invention in which the sample is moved backwards and forwards in a chamber between different temperature zones to achieve the required thermo-cycling.

As an alternative to low reaction volume chambers as described above for carrying out PCR monitoring in a stationary sample, the sample for PCR monitoring may be caused to flow through a channel or chamber of a microfluidic device and as it flows is subjected consecutively to different temperatures whereby thermo-cycling for PCR is achieved. Thus, for example, the sample may be caused to flow through a channel or chamber which passes consecutively through different temperature zones suitable for the PCR stages of denaturing, primer annealing and primer extension, e.g. a channel in a microfluidic device, e.g. a silicon chip device, which passes consecutively through zones of different temperature provided in the base suitable for successive repeats along the channel of the PCR stages of denaturing, primer annealing and primer extension. Such microfluidic structures for performing continuous flow nucleic acid amplification on a chip are described, for example, by Auroux et al. in 'Minaturised nucleic acid analysis' Lab Chip (2004) 4, 534-546 and may be combined with ISFET monitoring of amplification. Microfluidic structures of this type as illustrated in FIGS. 10 and 11 may be fabricated through the use of standard microfabrication techniques using for example photolithography to define the fluidic network and then an etching or deposition step to create the required channel or channels, for example in a PMMA, acrylic, Perspex™ or glass substrate. A cover plate in glass or PMMA or other material may or may not be overlaid to cover the channels. The base of the channel(s) may be formed by substrate bonding to a silicon chip with integrated ISFET and temperature sensors as well as heating or heat pump (Peltier) elements, such that the reaction mixture is in direct contact with these sensors and actuators, and may or may not include circuitry for temperature control. Alternatively, the base of the channel(s) may be formed by a printed circuit board (PCB) housing ISFET and temperature sensors such that these are in direct contact with the reaction mixture. The surface of the PCB will need to be leveled such that it provides a planar base onto which the microfluidic platform can be overlaid. The PCB may also house heating or heat pump elements, sensor interface and temperature control circuitry. Reagents present within the microfluidic channel or chamber will be those of the buffered amplification mixture, including the primers chosen for ability to hybridise to the target at sites suitable for amplification of the chosen sequence, the required enzyme(s) for amplification and all four dNTPs in excess.

Thus, in one embodiment for monitoring of PCR with thermo-cycling in accordance with the invention, the sample for nucleic acid amplification is caused to flow through a microfluidic channel (22) (e.g. microfabricated in a platform of acrylic, PMMA or Perspex) on a substrate (23), e.g. a silicon substrate of a silicon chip, and as it flows consecutively passes through temperature zones provided in the substrate or base suitable for successive repeats along the length of the channel of the stages of denaturing, annealing and chain extension, e.g. 95° C. for denaturation, 55° C. for primer hybridisation to target and 72° C. for primer extension with subsequent repetition (see FIG. 10). In this way, continuous flow-through amplification is achieved and may be monitored in accordance with the invention by means of one or more ISFETs embedded in the base. It may be preferred to employ ISFET detectors at a number of positions along the channel of a device as described above for continuous flow PCR such that real time PCR analysis can be achieved as amplification proceeds.

On-chip heating elements, such as polysilicon resistors may be used to heat the reaction mixture, using the Joule heating effect of power dissipated in a resistor when current is passed through it (P=I2R). Cooling could be achieved through heat dissipation through the silicon substrate and microfluidic platform, which is possible because of the small volumes of reaction mixture involved as well as the efficient thermal dissipation of the silicon chip base. Alternatively, an on-chip Peltier heat pump element for both heating and cooling could be implemented in known manner. Temperature uniformity is very important to avoid on-chip thermal gradients, both for the sake of the reaction mixture and for the sake of the ISFET and other on-chip circuitry. This may be achieved by an appropriate arrangement of the heating elements.

Temperature control could be achieved by a proportional-integral-derivative (PID) controller, which is one of the most common closed-loop feedback control systems. Errors between the measured temperature and the target temperature are used to calculate the level of heating required. Calculation of this output level is performed based on the current error directly (proportional), the history of the error (integral), and the predicted future error based on its rate of change (derivative). Similarly, a PI controller would stabilise temperature based on present and historical values of the error as described in Iordanov et al. (2004) ibid. Alternatively, techniques such as pulse-width modulation or duty-cycling could be implemented. In these techniques, heater output is not adjusted by amplitude but by time for which the heater is "on" as a percentage of a fixed time period. The "on" time is inversely proportional to the error between the measured temperature and the target temperature, so as the target temperature is approached, the "on" time of the heating element is also reduced.

It may alternatively be chosen to have a reciprocating system (see FIG. 11) whereby the amplification mixture is moved backwards and forwards in a microchamber between the required temperature zones for thermo-cycling. It will be appreciated that nucleic acid amplification resulting from such on chip sample-shunting PCR (described in the above-noted review article of Auroux et al.) may be monitored by providing an ISFET in a wall of the microfluidic chamber.

For further details of microfluidic devices for PCR, which may be modified for ISFET sensing in accordance with the invention, reference may again be made to Zhang et al. (2006) Biotech. Adv. 24, 243-284. As discussed in that review article, while such devices may preferably take the form of silicon chips, other materials for the chip substrate may be employed such as glass, various polymers and ceramics. As an alternative to contact heating for thermo-cycling, various non-contact heating methods may be employed as also discussed in the same review article, including by way of example hot-air mediated heating, utilisation of IR light, laser-mediated heating, induction heating and microwave irradiation While the above described PCR systems are designed to achieve thermo-cycling, various isothermic nucleic acid amplification techniques are known, e.g. single strand displacement amplification (SSDA), and DNA or RNA amplification using such techniques may equally be monitored by ISFET detection in accordance with the invention.

Apparatus

It will be appreciated that in a further aspect of the invention, there is provided a sensing apparatus for monitoring nucleic acid amplification in a sample in accordance with the invention wherein said apparatus comprises a chamber or channel to receive the sample in or on a base, e.g. a silicon substrate, and one or more pH sensitive ISFETs are arranged for monitoring of nucleic acid amplification in said chamber or channel, said base as presented in said chamber or channel having a coating to improve amplification efficiency, i.e. said base has been subjected to surface passivation as discussed above. The chamber or channel will generally be provided in a microfluidic device. The microfluidic device may take any form as discussed above. Need for surface passivation of the base may however be avoided by choice of base material or if dynamic passivation is employed as already noted above.

Thus, the invention also provides more generally a sensing apparatus for monitoring nucleic acid amplification in a sample wherein said apparatus comprises a microfluidic device in which a chamber or channel to receive the sample is provided in or on a base, e.g. a silicon substrate, and one or more pH sensitive ISFETs are arranged for monitoring of nucleic acid amplification in said chamber or channel. A low reaction volume chamber or well as discussed above may be provided for monitoring PCR in a stationary sample or a chamber or channel for continuous flow PCR. Further chambers or channels may be provided for simultaneous monitoring of multiple samples. As discussed above, the base may include heating elements and temperature sensors for thermocycling of the sample.

Monitoring of DNA Extension on Beads

Whether a pH sensitive ISFET is being used for DNA sequencing or nucleic acid amplification, e.g. qPCR, as an alternative to DNA extension being on DNA immobilized at the ISFET surface, DNA extension may occur on beads. Use of beads may be advantageously combined with use of an ISFET lying in a horizontal plane at the bottom of the reaction chamber or channel, e.g. as shown in FIG. 8, such that the beads settle in the vicinity of the ISFET sensing surface. The beads may be chosen such that gravitational settlement alone brings the beads into the vicinity of the ISFET sensing surface. Alternatively, magnetic/metallic beads may be employed and magnetically drawn into the vicinity of the ISFET sensing surface. The beads may be spherical particles synthesised from any suitable material for the attachment of DNA, e.g. silica, polystyrene, agarose or dextran. The size of the beads may be adjusted to assist gravitational settling and to accord with need to avoid blockage of the reaction chamber and entry and exit ports. The beads can be washed off the sensor surface using water or buffer solution. Linkage of DNA to the beads may be achieved using conventional methods, e.g. functionalization of the bead surface. A spacer may be employed. The coverage of the bead is controlled by adjusting the DNA to bead ratio. Where a pH sensitive ISFET is being used for DNA sequencing or monitoring of nucleic acid amplification and there is less size constraint, then, for example silica beads (e.g. about 200 nm diameter) may be preferably employed and DNA directly immobilized on the beads or immobilized following modification of the beads to provide a carboxylic functional group. Plastic beads (e.g. plastic microbeads of about 1 μm) may for example alternatively conveniently be employed. Where the ISFET is being employed to monitor nucleic acid amplification, the beads may carry probe DNA which captures target DNA in the sample.

Use of DNA Probe Immobilised on the ISFET

As an alternative to the use of beads, DNA probe for capture of target DNA may be linked directly or indirectly to the ISFET. Such immobilisation of DNA probe may be achieved using techniques well known for DNA probe immobilisation on a solid surface, e.g. such techniques well known from the DNA microarray art. Thus, DNA probe immobilisation on the ISFET may be achieved by in situ-oligonucleotide synthesis (by lithography or other means).

Sample Preparation for Amplification

Immobilisation of target probe as discussed above may be particularly favoured where the sample contains both target nucleic acid and unwanted nucleic acid. Immobilization of the probe will be such as to enable separation of target from any unwanted nucleic acid or interfering proteins. By use of immobilised probe to bring the target into close proximity with the ISFET sensing surface benefit may be achieved of increasing signal to noise ratio by localising the pH change caused by nucleic acid amplification.

DNA for amplification may come from a variety of sources such as a mouth swab, a blood sample or cultured cells. Sample preparation for monitoring of nucleic acid amplification in accordance with the invention may include one or both of the steps of concentrating cells and release of the nucleic acid required for amplification from the cells, e.g. a cloned DNA sequence. These steps may be carried out separate from the device for nucleic acid amplification or integrated into part of the same device, e.g. a PCR chip as described above. Released nucleic acid for amplification may, for example, be further purified by binding to microparticles (beads) as described above. Thus extraction and purification of target DNA from a biological sample might be achieved on the same chip as PCR by employing an appropriate lab-on-the chip (LOC) method such as the laser-irradiated magnetic bead system (LIMBIS) as described in Lee et al., 'Microchip-based one step DNA extraction and real time PCR in one chamber for rapid pathogen identification', Lab Chip (2006) 6, 886-895.

Kits

In a still further aspect of the invention, there are provided kits for detecting a target nucleic acid sequence in a sample by nucleic acid amplification, e.g. qPCR, which comprise a sensing device comprising a reaction chamber or channel and a pH sensitive ISFET for monitoring of nucleic amplification in said reaction chamber or channel as described above, e.g. such a sensing device in the form of a microfluidic chip, wherein primers for said amplification are provided in the reaction chamber or channel or separately within the kit. The primers may be provided together with bead-immobilized oligonucleotide probe for the target nucleic acid. As indicated above, the reaction chamber or channel of the sensing device may have other reagents dried within the reaction chamber including DNA polymerase and the required dNTPs for primer extension.

The following references provide additional background information relevant to the invention:

Shakhov and Nyrén, 'A Sensitive and Rapid Method for Determination of Pyophosphate Activity', Acta Chem. Scand. B 36 (1982) 689-694;

R. Buck, 'Electrochemistry of Ion-Selective Electrodes', Sensors and Actuators (1981) 1, 197-260;

Victorova et al, 'New substrates of DNA polymerases', FEBS Let. (1999) 453, 6-10; and Hanazato et al., 'Integrated Multi-Biosensors Based on an Ion-sensitive Field-Effect Transistor Using Photolithographic Techniques', IEEE Transactions on Electron Devices (1989) 36, 1303-1310.

The following example describes in more detail simulation of pH change with PCR cycles of DNA amplification and how this may be utilised for ISFET detection of target amplification.

Example

FIG. 7 shows pH change with PCR cycles for a typical PCR amplification employing an amplification mixture of 10 µM Tris HCl, pH 7.5, 0.4 mM dNTPs, 2 mM MgCl2, 50 mM KCl, 0.05% w/v BSA, 1 U per µl Taq polymerase, 1 µM PCR primer pair, and prepared DNA template (150-150,000 copies). The hypothetical amplicon is 200 base-pairs and each dNTP incorporation releases one proton. The starting pH value is 7.5. Given the concentration of the Tris and dNTP, the buffer capacity at each pH value can be determined. The theoretical pH change can be determined by the number of protons released from the reaction and the buffer capacity at the pH where the reaction occurs.

As indicated above, the number of cycles before the pH change passes a given threshold will depend on the DNA template concentration, the higher the concentration the fewer the cycles thereby allowing quantification of template DNA by calibrating the number of PCR cycles to reach the threshold against known template loads.

Calculation of Theoretical pH Change

In a simplified version of the reaction, a single extension reaction can be described as below:

$$HP_3O_{10}^{3-}\text{-nucleoside} + DNA\text{-}3'OH \Rightarrow H_2P_2O_7^{2-} + DNA\text{-}O\text{-}PO(O^-)\text{-}O\text{-nucleoside} \quad (1)$$

$$H_2P_2O_7^{2-} \Rightarrow HP_2O_7^{3-} + H^+ \quad (2)$$

The immediate element balance of the nucleotide insertion reaction is shown in (1), resulting in an extended DNA chain and pyrophosphate with a net charge of −2 (pKa1 and pKa2). In the pH range 6 to 8.5, some pyrophosphate will have the third proton (pKa3) dissociated as shown in (2), resulting in a decrease in pH.

pKa of pyrophosphates:

$pKa_1 \sim 0.83$ $pKa_2 \sim 1.96$ $pKa_3 \sim 6.68$ $pKa_4 \sim 9.39$

The calculation of pH change as the function of PCR cycle in a simplified version: Buffer capacity $$\beta = \frac{dn}{dpH},$$

where dn is the increase of base and dpH is the change of pH value. Also $$\beta \cong 2.303 \left( \frac{[HA]_0 K_a [H^+]}{(K_a + [H^+])^2} \right),$$

where $[HA]_o$ is the total concentration of the buffer chemical, such as TrisHCl, dNTP, DNA; Ka is the dissociation constant of the proton of the chemical; $[H^+]$ is the proton concentration.

Given the initial pH value of the reaction 7.5, one can work out the total buffer capacity of the reaction mixture of 150 copies DNA, 10 µM TriHCl and 400 µM dNTP, $\beta = \beta_{Tris} + \beta_{dNTP} = 1.08 \times 10^{-4}$ M (DNA concentration is negligible)

Then $$pH_2 = pH_1 + \beta \times dn$$
$$= 7.5 + \frac{dn}{1.08 \times 10^{-4}}$$

Then a new buffer capacity can be calculated based on the new starting pH value and the anticipated pH change given the amount of proton produced.

What is claimed:

1. A method of detecting a target nucleic acid by monitoring nucleic acid amplification in a sample comprising a buffered nucleic acid amplification mixture for amplification of a sequence of the target nucleic acid if present in the sample, characterised in that said monitoring comprises detecting a change of pH resulting from proton release in the presence of the target sequence as amplification proceeds beyond a threshold number of cycles to produce multiple copies of the target sequence such that buffering capacity of the sample is overcome, said detecting employing a sensing apparatus comprising an ISFET having a sensing surface exposed to the sample and arranged to generate an electrical output signal in response to the change of pH at said transistor surface and a detector for the electrical output signal from the ISFET, and wherein detection of the change of pH once the buffering capacity is overcome correlates with detection of the target nucleic acid.

2. The method of claim 1 wherein said nucleic acid amplification is polymerase chain reaction (PCR) amplification.

3. The method of claim 1 wherein the ISFET is provided with a layer of silicon nitride.

4. The method of claim 3 wherein a DNA polymerase enzyme linked layer is provided over the layer of silicon nitride.

5. The method of claim 1 wherein a reference electrode is employed.

6. The method of claim 1 wherein the target nucleic acid for amplification is captured on beads and nucleic acid amplification occurs on the beads which are brought into the vicinity of the ISFET sensing surface.

7. The method of claim 1 wherein said ISFET sensing surface is exposed to said sample in a low volume reaction chamber of 1 pl to 10 μl.

8. The method of claim 7 wherein said reaction chamber is in a microfluidic device comprising one or more further identical chambers containing said ISFET whereby nucleic acid amplification can be monitored simultaneously in more than one sample.

9. The method of claim 2 wherein the sample for PCR monitoring is caused to flow through a channel or chamber of a microfluidic device and as it flows is subjected consecutively to different temperatures whereby thermocycling for PCR is achieved.

10. The method of claim 9 wherein said sample is caused to flow through a chamber or channel which passes consecutively through different temperature zones suitable for said thermocycling.

11. The method of claim 10 wherein said sample is caused to flow through a channel which passes consecutively through different temperature zones provided in the base of said microfluidic device, said zones being suitable for successive repeats along the channel of the PCR stages of denaturing, primer annealing and primer extension.

12. The method of claim 11 wherein more than one ISFET is employed for sensing of pH change of the sample at different positions along said channel.

13. The method of claim 9 wherein said sample is moved backwards and forwards in a microchamber between required temperature zones for thermocycling and said ISFET is provided in a wall of said chamber.

14. The method of claim 1 wherein target nucleic acid for amplification is captured by probe immobilized on the ISFET.

15. The method of claim 7 wherein said reaction chamber is on a chip which includes resistive on-chip heating elements and temperature sensors whereby said chamber is capable of being heated and cooled for PCR thermocycling.

16. The method of claim 15 wherein said chip additionally includes on-chip temperature control circuitry.

17. The method of claim 1 wherein the number of amplification cycles used to reach said threshold number of cycles is used to quantify the amount of target sequence present in the sample.

18. The method of claim 1 wherein said nucleic acid amplification is isothermic.

19. A method of monitoring nucleic acid amplification in a sample comprising a buffered nucleic acid amplification mixture for amplification of a sequence of the target nucleic acid if present in the sample, characterised in that said monitoring comprises detecting a decrease in pH resulting from proton release in the presence of the target sequence as amplification proceeds beyond a threshold number of cycles to produce multiple copies of the target sequence such that buffering capacity of the sample is overcome, said detecting employing a sensing apparatus comprising an ISFET having a sensing surface exposed to the sample and arranged to generate an electrical output signal in response to the decrease in pH at said transistor surface and a detector for the electrical output signal from the ISFET.

20. The method of claim 19 wherein the number of amplification cycles used to reach said threshold number of cycles is used to quantify the amount of target sequence present in the sample.

* * * * *

SEQUENCE LISTING

<160> NUMBER OF SEQ ID NOS: 1

<210> SEQ ID NO 1
<211> LENGTH: 9
<212> TYPE: DNA
<213> ORGANISM: Artificial
<220> FEATURE:
<223> OTHER INFORMATION: DNA template for sequencing

<400> SEQUENCE: 1 gcctgctgc                                                      9